(12) United States Patent
Greenwood et al.

(10) Patent No.: US 6,516,799 B1
(45) Date of Patent: Feb. 11, 2003

(54) INHALATION COUNTER DEVICE

(75) Inventors: Mark H. Greenwood, Arlington Heights, IL (US); Mariann C. Straub, Winnetka, IL (US); Gabriel Rodriguez, Jr., Spring Grove, IL (US)

(73) Assignee: Sapphire Design, Inc., Park Ridge, IL (US)

( * ) Notice: Subject to any disclaimer, the term of this patent is extended or adjusted under 35 U.S.C. 154(b) by 0 days.

(21) Appl. No.: 09/391,169

(22) Filed: Sep. 8, 1999

(51) Int. Cl.[7] ............................................. A61M 15/00
(52) U.S. Cl. ............................ 128/203.12; 128/203.15; 128/203.19; 604/58
(58) Field of Search ....................... 128/203.12, 200.23, 128/203.15, 203.19, 203.23; 116/308, 307; 604/58

(56) References Cited

U.S. PATENT DOCUMENTS

| | | |
|---|---|---|
| 165,054 A | 6/1875 | Baldwin |
| 3,119,557 A | 1/1964 | Chapman |
| 4,565,302 A | 1/1986 | Pfeiffer et al. |
| 4,817,822 A | 4/1989 | Rand et al. |
| 5,020,527 A | 6/1991 | Dessertine |
| 5,300,042 A | 4/1994 | Kossoff et al. |
| 5,411,173 A | 5/1995 | Weinstein |
| 5,421,482 A * | 6/1995 | Garby et al. .................. 222/36 |
| 5,482,030 A | 1/1996 | Klein |
| 5,564,414 A | 10/1996 | Walker et al. |
| 5,740,792 A | 4/1998 | Ashley et al. |
| 5,799,651 A * | 9/1998 | Garby et al. ........... 128/200.23 |
| 5,829,434 A * | 11/1998 | Ambrosio et al. ..... 128/203.15 |
| 6,082,358 A * | 7/2000 | Scarrott et al. ........ 128/205.23 |

FOREIGN PATENT DOCUMENTS

| | | | |
|---|---|---|---|
| GB | 2195544 | * | 4/1988 |
| GB | 2348928 | | 4/1999 |
| WO | WO 00/59806 | | 3/2000 |

* cited by examiner

Primary Examiner—John G. Weiss
Assistant Examiner—Mital Patel
(74) Attorney, Agent, or Firm—Olson & Hierl, Ltd.

(57) ABSTRACT

The present invention discloses an inhalation device for dispensing a medicament. The device includes a housing defining a lumen, and level indicator and dose indicator devices both of which are operably associated with the housing. The level indicator device linearly indicates a remaining amount of medicament, while the dose indicator device indicates a number of doses dispensed for a predetermined time period.

30 Claims, 8 Drawing Sheets

INHALATION COUNTER DEVICE

TECHNICAL FIELD OF THE INVENTION

This invention relates to an inhalation device and specifically to an inhalation device that indicates both the level of the medicament and the number of doses dispensed over a predetermined period.

BACKGROUND OF THE INVENTION

It is well known to treat patients with medicaments contained in an aerosol, for example, in bronchodilation therapy. The aerosol can be conveniently administered to a patient by means of an inhalation device comprising a tubular housing or sleeve for holding the aerosol container and an outlet tube leading out of the tubular housing. The aerosol dispensers used in such inhalation devices typically are sold in 100 and 200 dose sizes and have an outlet valve member at one end which can be opened either by depressing the valve member while the dispenser is held stationary or by depressing the dispenser while the valve member is held stationary.

In use, the aerosol dispenser is placed in the tubular housing with the outlet valve member of the dispenser communicating via a support with the outlet tube, for example, a nozzle or mouthpiece. When used for dispensing medicaments, for example in bronchodilation therapy, the housing is held by the patient in a more or less upright condition with the mouthpiece or nozzle of the inhalation device placed in the mouth of the patient. The aerosol container is pressed towards the support to dispense a dose of medicament from the container which is then inhaled by the patient.

Patient compliance with a doctor's instructions on prescribed medication is extremely important in the treatment of medical disorders. Although the rate of compliance is higher when the patient must return to the hospital or physician's office to receive the medication, most drug treatment regimens require the patient to administer the drugs at regular intervals without supervision by hospital personnel, the patient's physician or other qualified medical personnel. Obviously, the treatment of a medical disorder will be frustrated if the patient does not administer the drugs as prescribed. In the past, physicians have had to rely on the patient's self-interest in his or her own well being to assure that drugs are properly administered as scheduled.

With anti-anxiety or sedative/hypnotics, such as valium and barbiturates, it is widely recognized that there is a real possibility that the patient will abuse or become dependent on the drug. Past studies have suggested that physicians should avoid the prescription of barbiturates because of the risk of dependence and the high toxicity of the drugs.

Furthermore, many such drugs have a narrow therapeutic range and can have severe side effects. It is well recognized that controlling the dosing of these types of drugs is important in mitigating problems with side effects. Many drugs can be extremely expensive (e.g., certain purified peptides and proteins). Controlling patient dosing of these drugs can also have economic benefits.

Metered dose inhalers, nebulizers and dry powder inhalers have been used for many years to treat pulmonary disorders such as asthma A metered dose inhaler typically comprises a canister pressure-fitted with a metering valve, where the canister is filled with an aerosol formulation that includes a drug dissolved or dispersed in a propellant together with a surfactant. Nebulizers are devices which include mechanical or electronic devices (e.g., a piezoelectric element) to atomize a drug suspension positioned in a containment cup. Nebulizers include an air or other gas source to deliver the atomized drug to the patient as a fine mist. Dry powder inhalers include mechanical or electronic devices to produce a fine mist from a powdered drug composition.

Patient non-compliance while using inhalation devices has been recognized as a major medical problem. It is generally believed that most patients underdose themselves. Furthermore, over use has been observed in various studies on days following visits to the physician's office.

Therefore, there is a need to improve patient compliance with prescribed dosing schedules. There is also a need for an inhalation device which can provide some assurance that a patient is not circumventing a dosing schedule by not inhaling the medicament.

A further disadvantage arising from use of currently available devices is that the patient cannot determine the amount of medicament in the aerosol container at any given time. In an extreme case this could mean that the patient, possibly suffering from severe bronchospasm and needing a dose of medicament, will find that the aerosol container will not dispense a dose because its contents have already been exhausted. There is a need for an inhalation device that avoids this problem.

SUMMARY OF THE INVENTION

The present invention relates to an inhalation device, that is either disposable or reusable. Specifically, the present invention provides an inhalation device that, when used with a medicament dispenser in any available dose size, indicates both the level of the medicament and the number of doses dispensed for a predetermined time period. In this manner, the present invention provides for easy and accurate dosage monitoring of the medicament, either as a single dose or multiple doses.

Examples of use of the inhalation device include delivery of a medicament to a patient's mouth, nostril, ear canal, or eye. The inhalation device can be used to dispense such drugs as beta-agonists such as albuterol (salbutamol), isoproterenol, ephedrine, epinephrine, salmeterol and terbutaline; corticosteroids such as triamcinolone acetonide, beclomethasone diproprionate, dexamethasone and aldosterone; allergic mediators such as cromcyln sodium; antibiotics; and anticholinergics. Moreover, these drugs can be dispensed by the inhalation device whether dissolved or dispersed in a propellant together with a surfactant or in a dry powder.

The inhalation device includes a generally tubular housing defining a lumen, a level indicator device and a dose indicator device. The housing terminates in a nozzle which defines a dispensing lumen terminating in a dispensing nozzle opening and further includes a replaceable cap.

The level indicator device is operably associated with the housing to indicate a remaining amount of the medicament in a liner fashion, while the dose indicator device is operably associated with the level indicator device and indicates the number of doses dispensed. In one particular embodiment, the level indicator and dose indictor devices include an advance ring operably associated with an advance tube. The advance tube has a helically wound groove operably associated with a level display device, and includes an indicia device operably associated with a display port to indicate the number of doses dispensed. Furthermore, the dose indicator device can be reset to zero so that the number of doses taken in any predetermined time period can be monitored.

Numerous other advantages and features of the present invention will become readily apparent from the following detailed description and from the accompanying drawings.

BRIEF DESCRIPTION OF THE DRAWINGS

In the drawings which form a part of the specification, and in which like numerals are used throughout to designate like parts.

DESCRIPTION OF PREFERRED EMBODIMENTS

Figure 1:
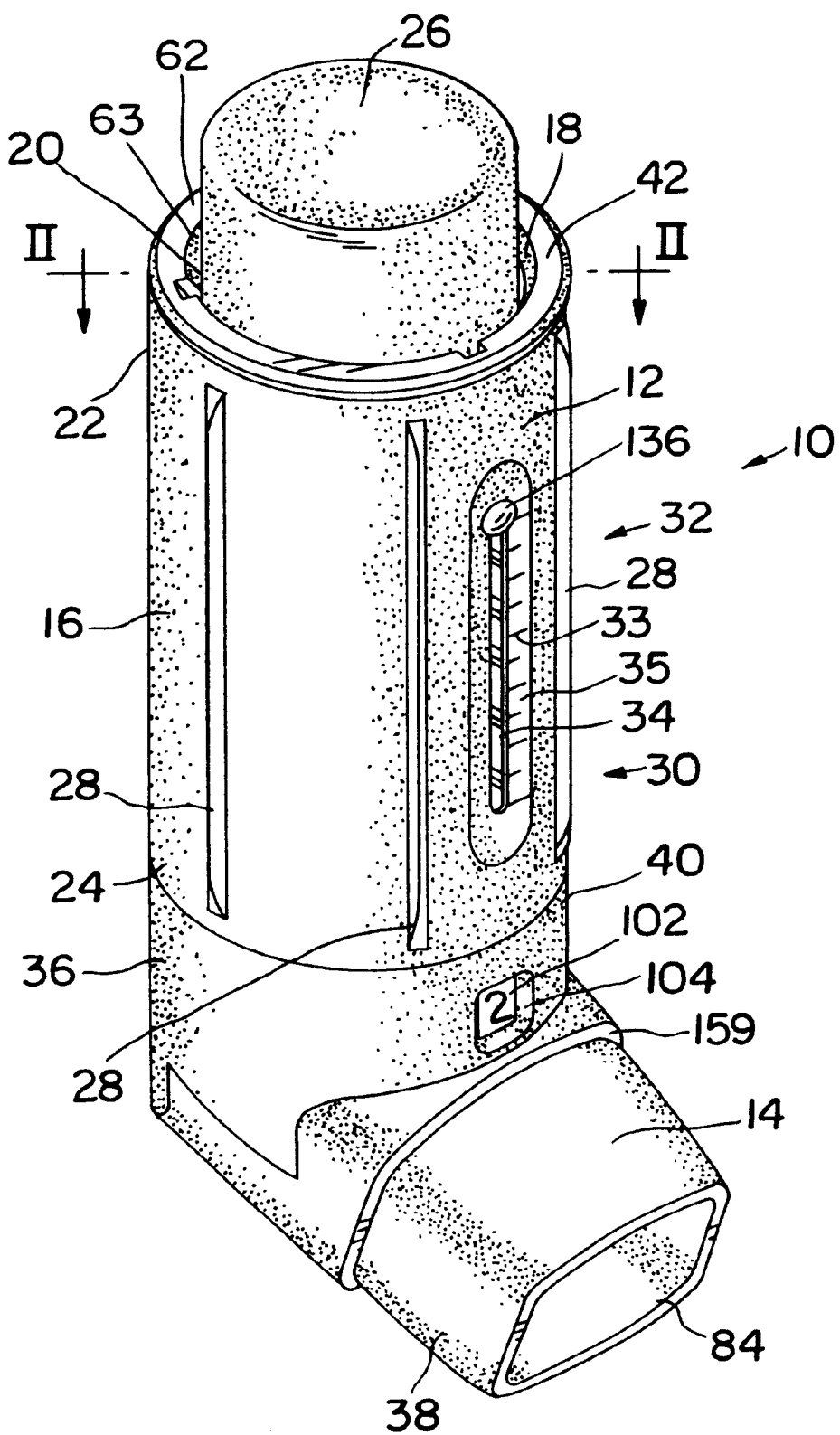
FIG. 1 is a perspective view of one embodiment of the subject inhalation device in accordance with the present invention.

While this invention can be embodied in many different forms, there are shown in the drawings and described in detail, preferred embodiments of the present invention. The present disclosure is an exemplification of the principles of the invention and is not intended to limit the invention to the embodiments illustrated.

Turning to FIG. 1, a perspective view of the subject inhalation device for dispensing a medicament, generally designated 10, is shown. The inhalation device 10 is comprised of a housing 12 and a nozzle 14 and is generally L-shaped when viewed from the side. Standing alone, the housing 12 has a tubular shape when viewed from the side (best seen in FIGS. 2, 6 and 8) and includes an outer surface 16 and an inner surface 18 defining a lumen 20.

Housing 12 is formed with proximal and distal ends 22 and 24, respectively, and is adapted to receive a medicament dispenser 26 in lumen 20. A plurality of ribs or fins 28 is integrally formed with and extend from outer surface 16. In the embodiment shown in FIG. 1, six fins 28 are shown equally spaced about housing 12, although other numbers and configurations are contemplated. Fins 28 provide a non-slip surface for gripping the housing 12 in addition to adding to the overall appearance.

The inhalation device 10 includes a level indicator device 30 operably associated with the housing 12 for indicating a remaining amount of the medicament. The level indicator device 30 further includes at least one level display device 32 operably associated with at least an advance tube and the housing 12. At least one slot 34 is defined in the housing 12 along a longitudinal axis thereof and in fluid communication with at least lumen 20, with the level display device 32 movably disposed therein and operably associated with the advance tube. In addition, the housing 12 further defines a concave engaging portion 35 in the outer surface 16 in proximity to the slot 34. Concave engaging portion 35 allows the level indicator device 32 to move in a linear fashion without interference from the user. In the embodiment depicted, slot 35 includes markings 33 to indicate the amount of medicament remaining in dispenser 26.

While one longitudinal slot 34, one concave engaging portion 35 and one level display device 32 are shown, other arrangements are contemplated. For example, two slots 34, each formed with a concave engaging portion 35, could be defined on opposing sides of the housing 12 with two level display devices 32 operably associated therewith. In this manner, the medicament level could be determined from opposing sides of the device 10.

FIG. 1 further reveals that the nozzle 14, intended for insertion into the mouth of a user, includes upper and lower portions 36 and 38, and is in operable communication with the housing 12 and the lumen 20. While the nozzle 14 is designed for insertion into the mouth, it is contemplated that it could be reconfigured and used with or inserted into the user's eye, nostril, ear or any other orifice. As shown, the upper portion 36 has a proximal end 40 snap-fitted to the distal end 24 of the housing 12, so that the nozzle 14 is in fluid communication with the lumen 20. Although a snap-fit is described, any means for rotably connecting the nozzle 14 to the housing 12 is contemplated, including an airtight friction fit, reciprocally spaced threads formed on the housing 12 and nozzle 14, screws, pins, etc.

Figure 2:
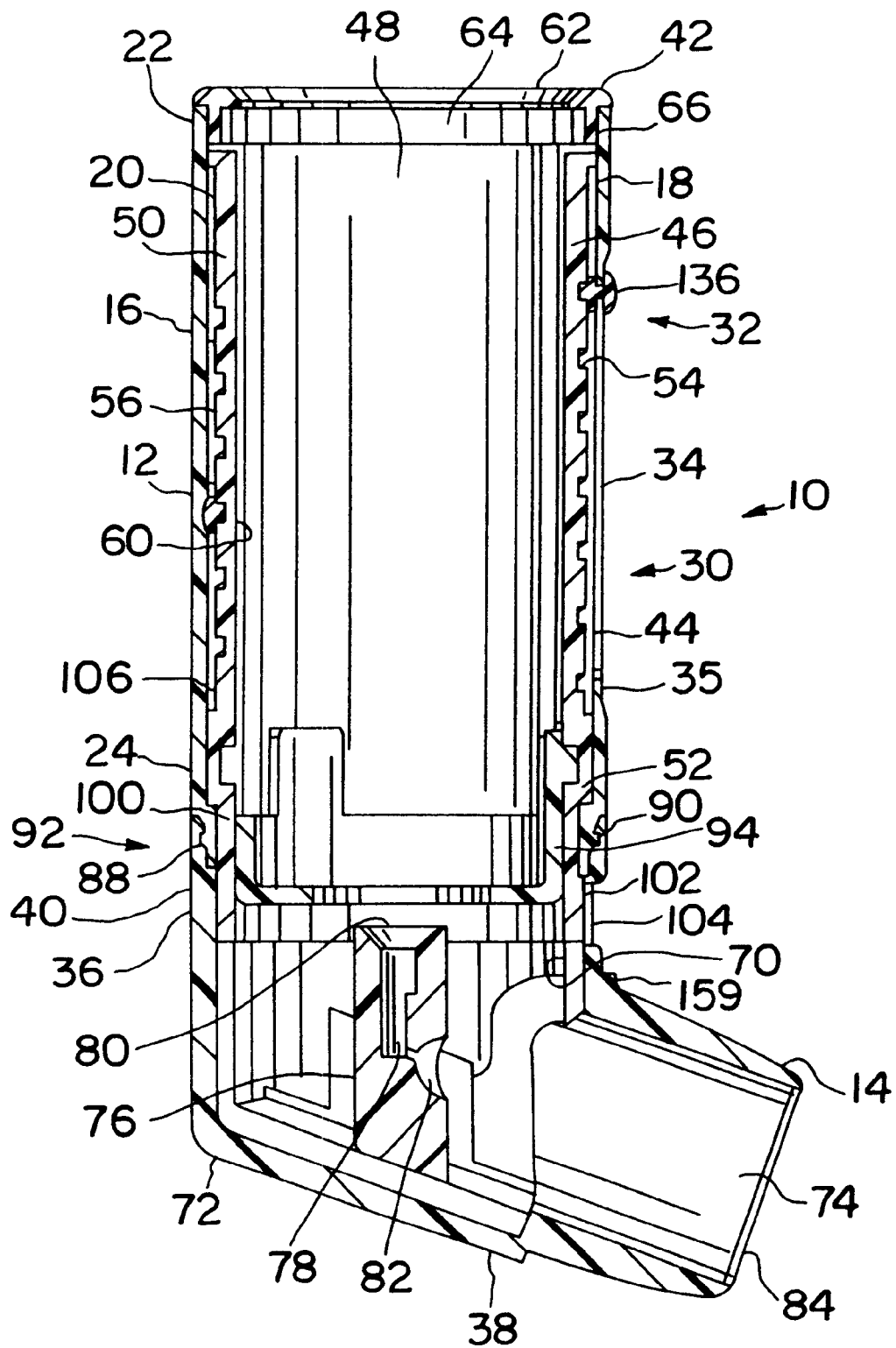
FIG. 2 is a side elevational view in cross-section of the Inhalation device of FIG. 1 taken substantially along line II—II.

Turning now to FIG. 2, a side elevational view of one embodiment of the inhalation device 10 is shown partially in cross-section. FIG. 2 reveals that the device 10 includes a top member or ring 42 (best seen in FIGS. 3 and 4) operably associated with at least the proximal end 22 of the housing 12. In one contemplated embodiment, top member 42 is operably associated with at least the housing 12, the level indicator device 30 and the medicament dispenser 26, to prevent the level indicator device 30 and/or the medicament dispenser 26 from becoming unintentionally or accidentally separated from the housing 12.

FIG. 2 further reveals that the level indicator device 30 includes at least an advance device 44 movably disposed within the lumen 20 of housing 12. In one preferred embodiment, advance device 44 comprises an advance tube 46 defining a tube lumen 48, having upper and lower tube portions 50 and 52, and which is rotatably disposed within the lumen 20 of housing 12.

At least one downwardly, helically wound groove 54 (best seen in FIGS. 9 and 11) is defined in the outer surface 56 of the advance tube 46 and is operably associated with the level display device 32 so that the level display device 32 is snap-fitted into groove 54. It is contemplated that medicament device 26 could be sold in a multiplicity of doses. Typically, the medicament dispenser 26 comes either in 100 or 200 doses, although other dose amounts are contemplated. It is therefore contemplated that the level indicator device 30 of the present invention must accommodate such different dose sizes. The angle, linear length and/or spacing of the helically wound groove 54 could vary depending on the dose size, i.e. 100 or 200 doses. Furthermore, while only one helically wound groove 54 is shown, two or more grooves are contemplated.

In addition, it is contemplated that advance tube 46 includes at least one linear groove 58 defined in the inner surface 60 in fluid communication with tube lumen 48. In one preferred embodiment shown in FIGS. 1 and 9, three grooves 58 are defined in and equally spaced about inner surface 60 along the longitudinal axis of the advance tube 56. The groove 58 is preferably operably associated with at least an advance ring as discussed below.

Figure 3:
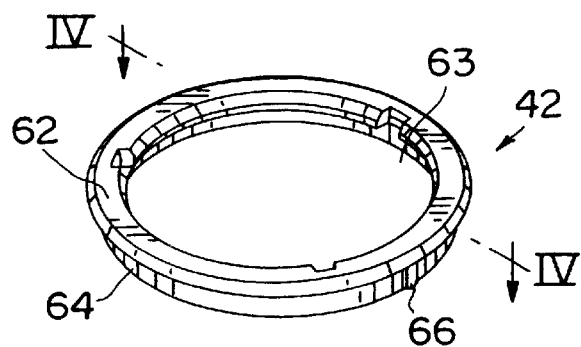
FIG. 3 is a perspective view of the top member of the inhalation device of FIG. 1.

Top member 42 is formed with a ring portion 62 with a skirt portion 64 generally downwardly depending therefrom which defines an aperture 63, where skirt portion 64 is formed with at least one generally outwardly extending member 66 (best seen in FIG. 3). Top member 42 is operably associated with at least the housing 12 so that ring portion 62 is in contact with and rests upon the proximal end 22, while the skirt portion 64 extends into the lumen 20. Extending member 66 operably engages at least one housing groove 68 (best seen in FIG. 5) defined in the inner surface 18, so that the medicament dispenser 26 is securably movably mounted in the lumen 20 and extends through the aperture 63. In one preferred embodiment, the top member 42 is operably associated with both the advance member 44 and the medicament dispenser 26, so that the medicament dispenser 26 and advance device 44 are securably movably mounted in the lumen 20. Furthermore, top member 42 assures that dispenser 26 is properly centered in lumen 48.

Provision is further made for removably connecting the nozzle 14 to the housing 12, so that the nozzle 14 is in rotatable, removable, operable communication with the lumen 20. FIG. 2 shows that the nozzle 14 includes nozzle inner and outer surfaces 70 and 72 respectively, and a nozzle lumen 74 defined by nozzle inner surface 70 so that nozzle lumen 74 is in fluid communication with the lumen 20. While only one nozzle lumen 74 is shown, a plurality thereof are contemplated, substantially co-axially aligned with each other and all in fluid communication with the lumen 20. Further, a plurality of flat panels 75 are defined about the circumference of inner surface 70 which operably engage a corresponding number of panels formed on housing 12.

As best shown in FIG. 1, medicament dispenser 26 may be inserted into the lumen 20 preferably by inserting medicament dispenser 26 into tube lumen 48 so that one end protrudes from the proximal end 22. Spacer ribs (not shown) may be provided inside advance tube 46 on, and spaced about, inner surface 60, so that the medicament dispenser 26 is held spaced therefrom. A support 76 is provided in the nozzle. 14 with at least one passageway 78 defined therein in fluid communication with at least lumen 20, so that the medicament dispenser 26 can be supported and located therein. In one preferred embodiment, support 76 defines a first opening 80 and second opening 82, with the passageway 78 in fluid communication with and extending between both the first and second openings 80 and 82. Furthermore, the first opening 80 is defined in proximity to and in fluid communication with the lumen 20, while the second opening 82 is in proximity to and in fluid communication with the nozzle lumen 74.

If the inhalation device 10 is used with medicament dispenser 26, the protruding portion or outlet valve member (not shown) of the medicament dispenser 26 is inserted into the first opening 80 and passageway 78, so that the dispenser is supported by the support 76. The outlet valve member of the medicament dispenser 26 can be depressed to move the dispenser 26 relative to the nozzle, thus opening a valve in the medicament dispenser 26 so that a premeasured dose of medicament will be discharged. One dose of medicament will be discharged each time the dispenser 26 is fully depressed. The medicament is discharged into the passageway 78 through second opening 82 into the nozzle lumen 74 from which it can be inhaled or otherwise delivered to the user through the nozzle opening 84.

Figure 5:
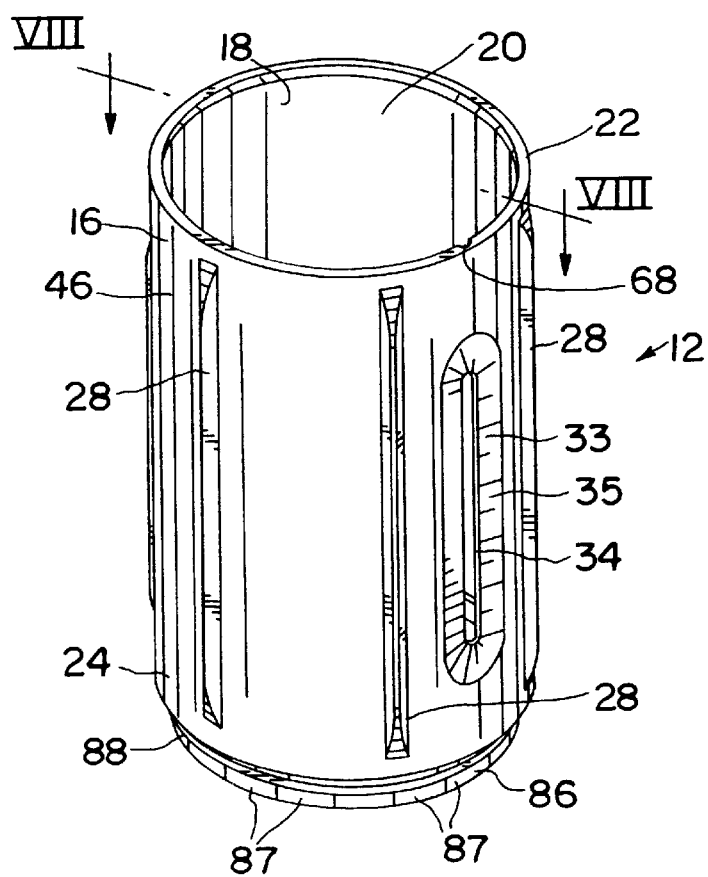
FIG. 5 is a perspective view of the housing of FIG. 1 with the top member and nozzle removed.
Figure 6:
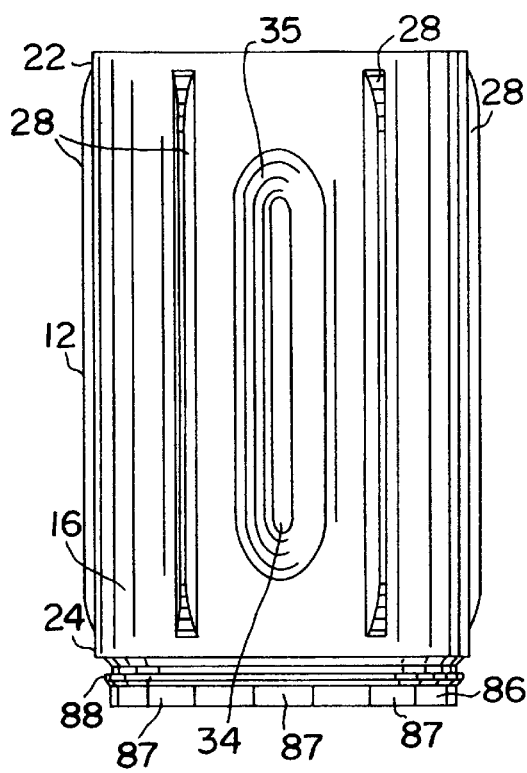
FIG. 6 is a side elevational view of the housing of FIG. 5.
Figure 7:
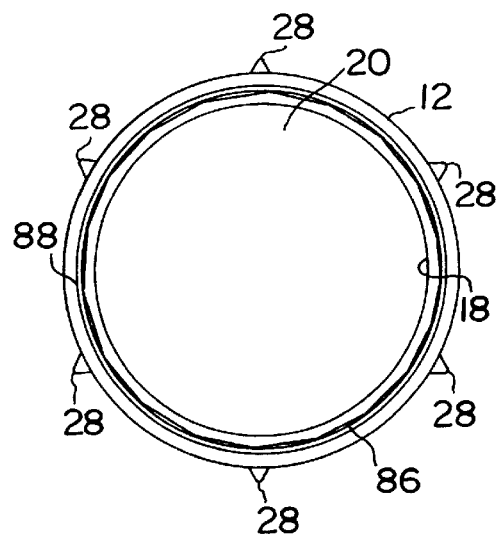
FIG. 7 is a bottom plan view of the housing of FIG. 6 showing the distal end of the extended ring portion.

An extended ring portion 86 is shown at the distal end 24 with a plurality of flat panels 87 formed thereon (best seen in FIGS. 5 and 6). Ideally, the extended ring portion 86 is joined to and integral with the housing 12 and is utilized to secure the nozzle 14 to the housing 12 in a snap-fit manner, so that the nozzle 14 is in fluid communication with the lumen 20. Extended ring portion 86 is formed with at least one connecting point, at least one lip 88 projecting generally radially outwardly from the extended ring portion 86, and extending around the circumference thereof While one lip 88 is shown, two or more lips 88 or even a plurality of generally radially outwardly extending nubs spaced about extended ring portion 86 are contemplated.

Correspondingly, at least one connecting point is formed on the nozzle 14. At least one annular groove 90 (best seen in FIGS. 16 and 18) is defined by the nozzle inner surface 70 extending around the inner circumference of nozzle proximal end 40. Groove 90 is in spaced relationship to and positionally aligned with lip 88, and so frictionally accommodates the lip. The groove 90 is defined to receive the lip 88 of the housing 12, so that the groove 90 and lip 88 act in concert to secure the nozzle 14 to the housing 12 in an airtight, snap-type friction fit. Again, while this snap-type friction fit is preferred, other securing means are contemplated for rotably securing nozzle 14 to housing 12.

As provided previously, extended ring portion 86 is formed with a plurality of panels 87 in numerical and positional relationship to the panels 75 of the nozzle 14. The panels 75 are aligned with and operably engage the panels 87. In one preferred embodiment, the extended ring portion 86 and nozzle 14 both include eighteen panels 87 and 75 respectively. The panels 87 and 75 cooperate to provide a slight friction therebetween that allows the nozzle 14 to rotate about the housing 12, similar to that of a watch bezel. Rotating the nozzle 14 allows the dose indicator device to be reset at the end of each predetermined period, whether daily, weekly, monthly, etc. The slight friction between panels 75 and 87 prevents such reset from occurring accidentally. That is, the operable engagement of panels 75 and 87 requires that the dose indicator device be deliberately reset by the user.

As shown in FIG. 2, an advance member 92 is disposed in the lumen 20 of housing 12 in operable communication with the advance device 44. In one preferred embodiment, the advance member 92 comprises an advance ring 94 having at least one projecting member 96 projecting therefrom and integral therewith, disposed within tube lumen 48. At least one serrated portion 98 (shown in FIG. 12) is defined in advance tube 48 in proximity to the distal end of tube lower portion 52, whereby the at least one projecting member 96 is operably associated with the at least one serrated portion 98.

Figure 4:
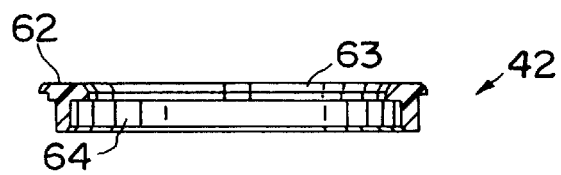
FIG. 4 is a side elevational view in cross-section of the top member of FIG. 3 taken substantially along line VI—VI.

Top member 42 is shown in greater detail in FIGS. 3 and 4, which provide both perspective and partial cross-sectional side elevational views of top member 42. Top member 42 has a circular shape when viewed from the top and is preferably formed of a surgical metal material or rigid plastic suitable for sterilization and reuse or disposal. Top member 42 is comprised of ring portion 62 having skirt portion 64 generally downwardly depending therefrom defining aperture 63, where skirt portion 64 is formed with at least one generally outwardly extending member 66.

Top member 42 is operably associated with at least the housing 12 so that ring portion 62 is in contact with and rests upon the proximal end 22, while the skirt portion 64 extends into the lumen 20. Extending member 66 operably engages the at least one housing groove 68 (best seen in FIG. 5) so that at least the medicament dispenser 26 is securably rotatably mounted in the lumen 20. In one preferred embodiment, top member 42 is operably associated with the medicament dispenser 26, so that the medicament dispenser 26 is properly positioned within the center of lumen 48 with the proximal end of the dispenser 26 extending through the aperture 63. Centering the medicament dispenser 26 allows it to rotate freely.

FIGS. 5–8 show various views of housing 12 with the top member 42 and the nozzle 14 removed, and include a perspective view, a side elevational view, a bottom plan view and a side elevational view in cross-section. Housing 12 has a generally rectangular, tubular shape when viewed from the side (best seen in FIGS. 6 and 8) and a circular shape when viewed from the bottom (best seen in FIG. 7). In one preferred embodiment, housing 12 is formed of surgical metal material or rigid plastic suitable for sterilization and reuse or disposal.

As shown in FIGS. 5–8, the housing 12 consists of outer surface 16 and inner surface 18 defining the lumen 20. Housing 12 is formed with proximal and distal ends 22 and 24 and is adapted for receiving the medicament dispenser 26 (not shown) in the lumen 20. In one embodiment, housing 12 is configured for removably and rotationally receiving the advance device 44 in lumen 20. However, it is also contemplated that advance device 44 is rotatably fixed within lumen 20. A plurality of ribs or fins 28 are integrally formed with and extend from the outer surface 16. In the illustrated embodiment, six fins 28 (best seen in FIG. 7) are shown equally spaced about housing 12, although other numbers and configurations are contemplated. Again, fins 28 provide a non-slip surface for gripping the housing 12 in addition to providing an attractive overall appearance.

Figure 8:
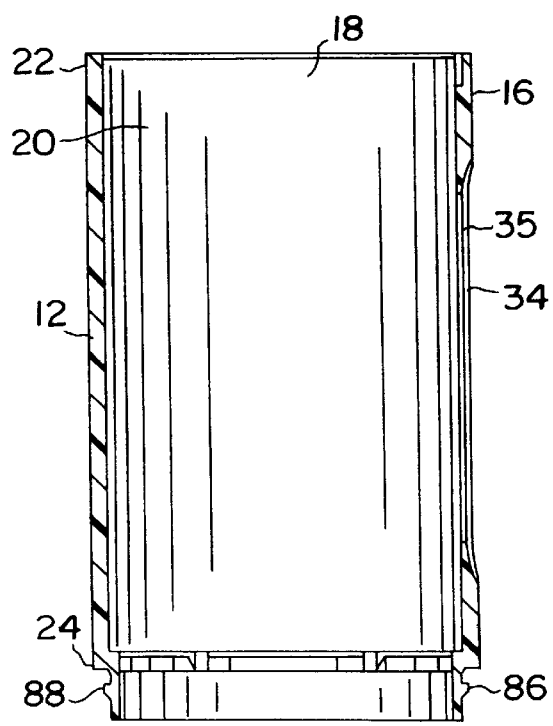
FIG. 8 is a side elevational view in cross-section of the housing of FIG. 5 taken substantially along line VIII—VIII.

FIGS. 6 and 8 demonstrate that the at least one slot 34 is defined in housing 12 along a longitudinal axis thereof and in fluid communication with at least lumen 20, so that the at least one level display device 32 may be movably disposed therein in a linear fashion and operably associated with the advance tube 46. Additionally, the housing 12 further defines a concave engaging portion 35 with markings 33 in the outer surface 16 in proximity to the slot 34. This slot 34 allows level display device 32 to freely move linearly therein. While one longitudinal slot 34 and concave engaging portion 35 are shown, other arrangements are contemplated.

FIGS. 1 and 2 reveal that the nozzle 14 is in operable communication with the housing 12 and the lumen 20. As shown, the upper portion 36 of nozzle 14 has a proximal end 40 snap-fitted to the distal end 24 of housing 12, so that the nozzle 14 is in fluid communication with the lumen 20. FIGS. 5–8 show the extended ring portion 86 at the distal end 24 of housing 12. Ideally, the extended ring portion 86 is joined to and integral with the housing 12 and is utilized to secure the nozzle 14 to the housing 12 in a snap-fit manner, so that the nozzle 14 is in fluid communication with the lumen 20. Although a snap-fit connection is described, any means for connecting the nozzle 14 to the housing 12 is contemplated, including an airtight friction fit, reciprocally spaced threads formed on the housing 12 and nozzle 14, screws, pins, etc.

Extended ring portion 86 is formed with at least one connecting point, the at least one lip 88 projecting generally radially outwardly from the extended ring portion 86, and the plurality flat panels 75, both of which extend around the circumference thereof. While one lip 88 is shown, two or more lips or even a plurality of generally radially outwardly extending nubs are contemplated.

As provided earlier, the at least one annular groove 90 which is in spaced relationship to and positionally aligned with the lip 88, is inset in the nozzle inner surface 70. The groove 90 extends around the inner circumference of nozzle proximal end 40 and frictionally accommodates the lip 88. The groove 90 is defined by inner surface 70 to receive lip 88 of the housing 12, so that the groove 90 and lip 88 act in concert to secure the nozzle 14 to the housing 12 in an air-tight, snap-type friction fit. Again, while this snap-type friction fit is preferred, other securing means are contemplated, including threads.

Nozzle 14 includes eighteen flat panels 87 that numerical and positionally correspond with the eighteen flat panels 75. The interaction of the groove 90 and lip 88 allow the nozzle 14 to rotate about housing 12, providing a means for resetting the dose indicator device. However, the operable interaction of flat panels 75 and 87 provides sufficient friction therebetween, acting like a rotating watch bezel, so that the rotation of nozzle 12 is deliberate.

Figure 9:
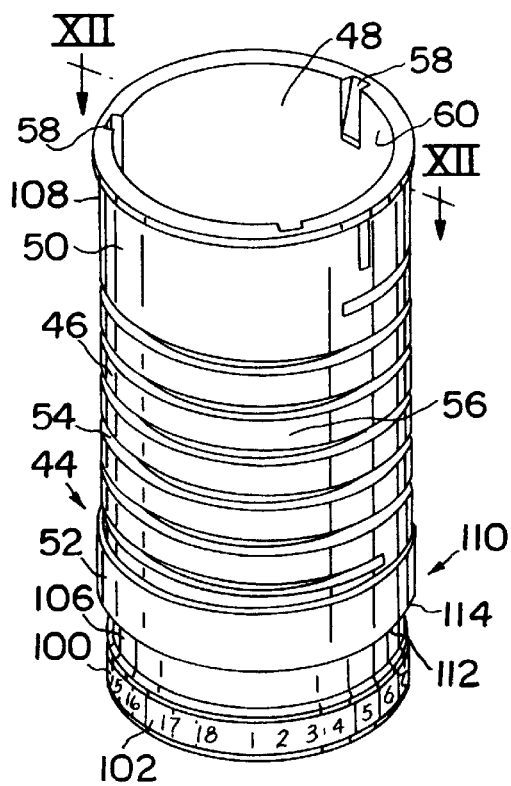
FIG. 9 is a perspective view of the advance tube of FIG. 1 removed from the housing and showing the indicia device.
Figure 10:
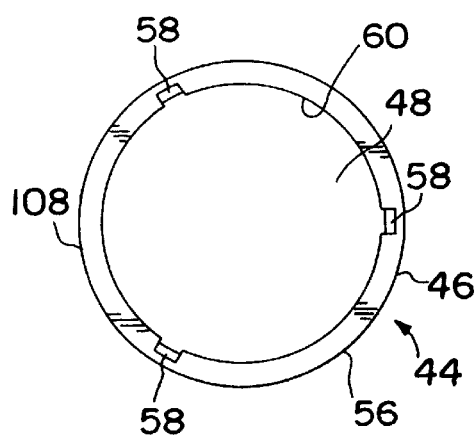
FIG. 10 is a top plan view of the advance tube of FIG. 9.
Figure 11A:
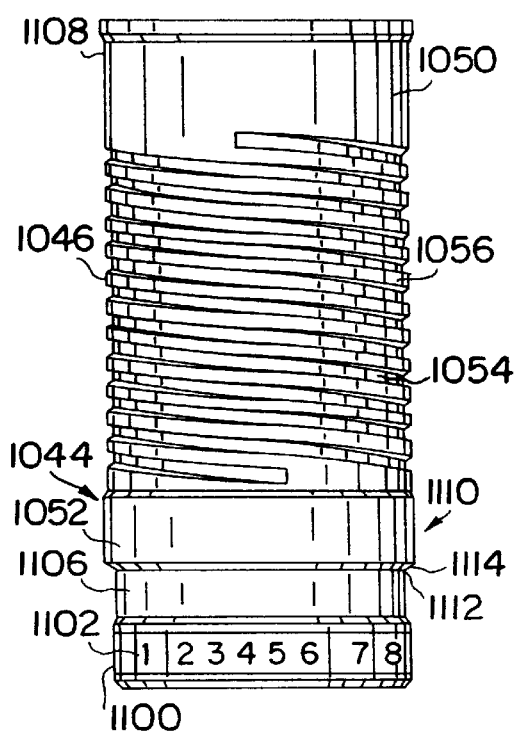
FIG. 11A is a side elevational view of an alternate embodiment of the advance tube of FIG. 11.
Figure 11:
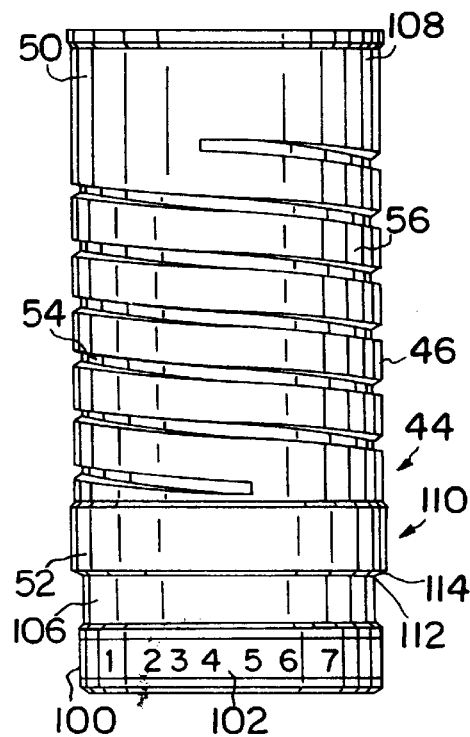
FIG. 11 is a side elevational view of the advance tube of FIG. 9 showing the indicia device.

Operation of the level indicator device 30, which preferably includes at least an advance device 44 movably disposed within the lumen 20 of housing 12, is better understood by reviewing FIGS. 9–11. In one preferred embodiment, advance device 44 comprises an advance tube 46 defining tube lumen 48, includes upper and lower tube portions 50 and 52, and is rotatably disposed within the lumen 20 of housing 12. FIG. 9 is a perspective view of advance tube 46 removed from the housing, FIG. 10 is a top plan view, FIGS. 11 and 11A are side elevational views, and FIG. 12 shows a side elevational view of the advance tube in cross-section.

FIGS. 9 and 11 reveal an indented portion 106 defined by outer surface 56 in proximity to distal end 100 of tube lower portion 52, in addition to the at least one downwardly helically wound groove 54 defined in outer surface 56, which is operably associated with level display device 32. In one preferred embodiment, the at least one level display device 32 is snap-fitted into the helically wound groove 54. While only one groove 54 is shown two or more grooves are contemplated each operably engaging a level display device 32, as discussed above.

Further, at least one groove 58 is defined in inner surface 60 and in fluid communication with tube lumen 48. In one preferred embodiment shown in FIGS. 9 and 10, three grooves 58 are defined in and equally spaced about inner surface 60 along the longitudinal axis of the advance tube 56. It is contemplated that the groove 58 extends continuously along the inner surface 60 between the proximal end 108 of tube upper portion 50 and serrated portion 98, and is preferably operably associated with at least the advance ring 94. However, in one preferred embodiment, the groove 58 extends only part way along the inner surface 60, providing a lead in for inserting advance ring 94 during assembly. The advance ring 94 is positioned in tube lumen 48 so that the at least one projecting member 96 operably engages the at least one groove 58. In one preferred, disposable, embodiment, advance ring 94 is fixedly connected to dispenser 26, held in place by gluing, bonding, crimping, a press-fit or the like. However, a reusable embodiment is also contemplated, where advance ring 94 is rotatably positioned in tube lumen 48. Three projecting members 96 are preferably in spaced relationship with the groove 58, so that the advance ring 94 slidably advances in tube lumen 48 in a linear fashion until the at least one projecting member 96 operably engages serrated portion 98.

Figure 12:
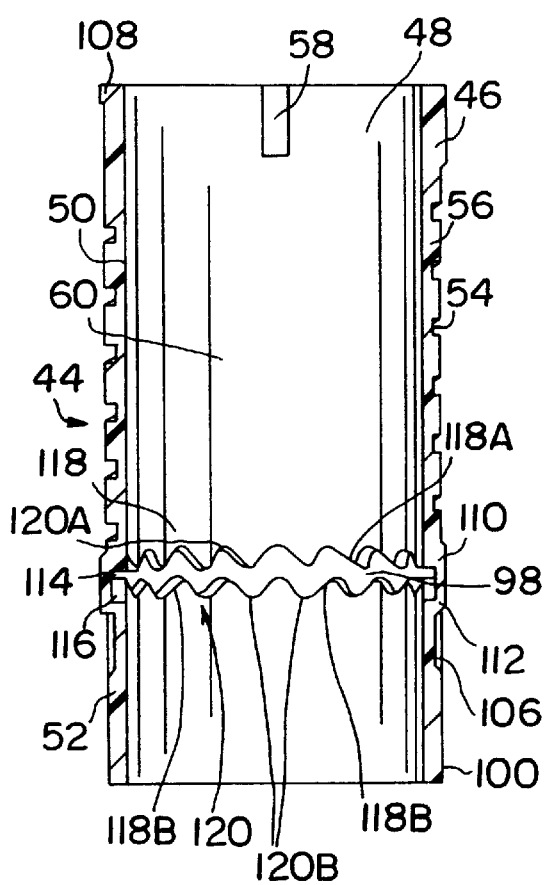
FIG. 12 is a side elevational view in cross-section of the advance tube of FIG. 9 taken substantially along line XII—XII showing the serrated portion defined by the upper and lower portions of the advance tube.

As provided above the advance tube 46 is formed of at least two parts, tube upper and lower portions 50 and 52, respectively, operably associated with each other (best seen in FIG. 12). Distal end 110 of tube upper portion 50 is operably associated with the proximal end 112 of tube lower portion 52. In the embodiment shown in FIG. 12, extended portion 114 formed by distal end 110 engages, or rests upon, the shoulder 116 defined by proximal end 112. While this method is preferred, other means of operably associating tube upper and lower portions 50 and 52 are contemplated, including threads, gluing, bonding and the like, in addition to forming advance tube 46 as a unitary piece.

Distal and proximal ends 110 and 112 define serrated portion 98, which is operably associated with the level and dose indicator devices. Advance member 94, which is disposed within tube lumen 48, has at least one projecting member 96 operably engaging teeth 118 (generally designated teeth 118 and including proximal and distal teeth 118A and 118B, respectively) of the serrated portion 98. Downward pressure on the advance member 92 causes the at least one projecting member 96 to move into, and press downwardly on, the grooves 120 (generally designated grooves 120 and including proximal and distal grooves 120A and 120B, respectively) defined between teeth 118. Releasing the pressure on advance member 92 causes the projecting member 96 to move upwardly to the tip of the next tooth in the series of teeth 118 and into the next groove, in a rachet-like fashion. Furthermore, as the at least one projecting member 96 engages the grooves 120, it causes the advance tube 46 to rotate in the lumen 20 in the opposite direction. Thus, in a preferred embodiment, applying (downward) pressure to advance ring 94, causes advance ring 94 to move in tube lumen 48 in one chosen direction in a rachet-like fashion, and correspondingly causes the advance tube 46 to rotate in the lumen 20 in the opposite direction, also in a rachet-like fashion.

Closer inspection of FIG. 12 reveals that the proximal and distal series of teeth 118A and 118B are offset. That is, proximal teeth 118A are in a spaced relationship with distal grooves 120B, while distal teeth 118B are spaced relationship with proximal grooves 120A. Downward pressure on the advance member 92 causes the at least one projecting member 96 to move into, and press downwardly on, the distal groove 120B defined between teeth 118B. Releasing the pressure on advance member 92 causes the projecting member 96 to move upwardly, hitting the proximal tooth 118A just slightly off-center, i.e., just off the tip of the proximal tooth 118A, then moving into and towards the top of the next proximal groove 120A in series, causing the advance tube 46 to rotate in the lumen 20 in the opposite direction.

FIG. 11A depicts an alternate embodiment of the advance tube 46 of FIG. 11. The elements in FIG. 11A designated by reference numerals in the 1000 series, having the last two or three digits in common with elements described above with respect to FIG. 11, correspond to and have similar functions or structure as the elements described above. At least one downwardly, helically wound groove 1054 is defined in the outer surface 1056 of advance tube 1046 and is operably associated with the level display device 1032, so that level display device 1032 is snap-fitted into groove 1054.

However, it is contemplated that medicament could be sold in a multiplicity of doses. Typically, the medicament dispenser 26 comes in 100 and 200 doses, although other dose amounts are contemplated. Therefore, it is contemplated that the level indicator device 1032 of the present invention must accommodate such different dose sizes. FIG. 11A depicts an advance tube 1046 able to accommodate dispensers 26 having such different dose size. The helically wound groove 1054 of FIG. 11A has a different angle, linear length and spacing than the helically wound groove 54 of FIG. 11. Further, while only one helically wound groove 1054 is shown, two or more grooves, each having a different angle, linear length, and spacing, and each able to accommodate different indicator devices 1032 are contemplated.

Figure 13:
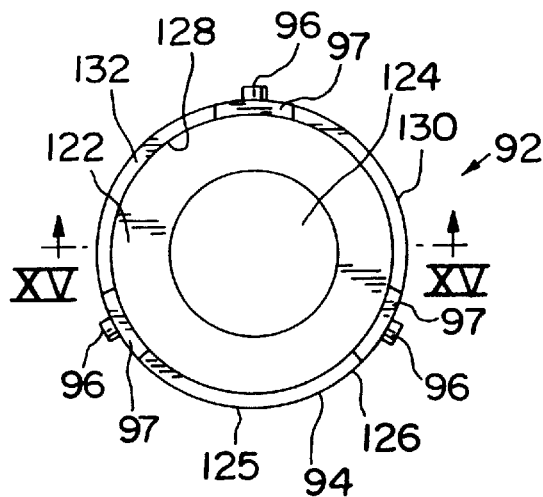
FIG. 13 is a top plan view of the advance ring.
Figure 14:
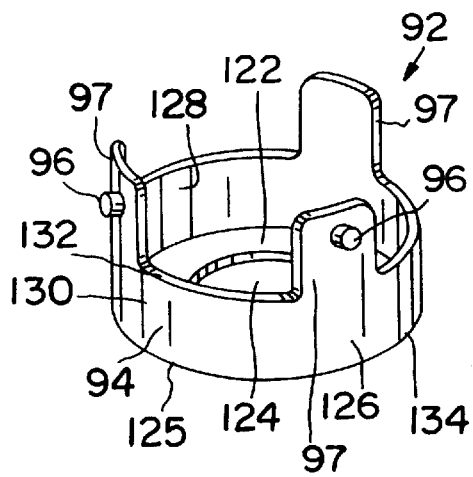
FIG. 14 is a side elevational view of the advance ring of FIG. 13.
Figure 15:
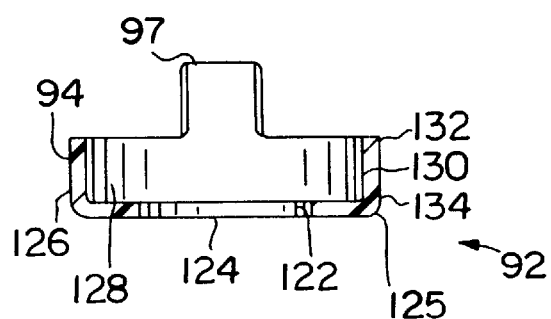
FIG. 15 is a side elevational view in cross-section of the advance ring of FIG. 13 taken substantially along line XV—XV.

FIGS. 13–15 provide further detail on the dose indicator device which comprises the advance member 94, which in one preferred embodiment is the advance ring 94. FIG. 13 is a top plan view, FIG. 14 is a side elevational view and FIG. 15 is a side elevational view in cross-section of the advance ring 94. In the illustrated embodiment, advance ring 94 has a generally circular shape when viewed from above, and is preferably made of surgical metal material or rigid plastic suitable for sterilization and reuse or disposal.

As shown in FIGS. 13–15, advance member 92 is movably disposed in lumen 48 in operable communication with the advance device 44. In one preferred embodiment, the advance member 92 comprises advance ring 94 having at least one but preferably three projecting members 96 extending therefrom and integral therewith disposed in the tube lumen 48 and operably associated with the advance tube 46. As shown, at least one projection tab 97 extends from each member 96. The advance ring 94 further includes a ring portion 122 defining at least one aperture 124 therein. While only one aperture 124 is shown, two or more apertures are contemplated depending on the particular medicament dispenser 26.

A wall portion 126 is shown extended generally upward from and integral with ring portion 122, so that the inner surface 128 of wall portion 126 and ring portion 122 define a cup-like structure (best seen in FIG. 15). Wall portion 126 runs along and extends from a peripheral edge 125 of ring portion 122, although other arrangements are contemplated. For example, wall portion 126 could run along and extend from the inner circumference of the ring portion 122 (around the aperture 124).

Projecting tabs 97 extend from and are integral with wall portion 126, while at least one projecting member 96 extends from and is integral with each member 96. As shown in FIG. 13, three projecting members 96 each having a projecting tab 97, that is equally spaced about and project from outer surface 130 at the proximal end 132. However, other arrangements are contemplated including having the projecting members 96 attached to any portion of the outer surface 130, including distal end 134, depending on the position of the advancing ring 94 in the lumen 48.

As set forth above, tube upper and lower portions 50 and 52 define the at least one serrated portion 98 in proximity to the proximal end 112 of tube lower portion 52. Projecting members 96 are operably associated with the at least one serrated portion 98. Preferably advance ring 94, which is disposed in tube lumen 48, has the projecting member 96 of each projecting tab 97 operably engaging teeth 118. Downward pressure on the advance ring 94 causes the projecting members 96 to move into, and press downwardly on, the grooves 120. Releasing the pressure on the advance ring 94 causes the projecting members 96 to move upwardly to the tip of the next tooth in the series of teeth 118 and into the next groove 120. Furthermore, as the projecting members 96 engage the grooves 120, they cause the advance tube 46 to rotate in the lumen 20 in the opposite direction, in a ratchet-like fashion. Thus, applying (downward) pressure on advance ring 94, causes the advance tube 46 to rotate in lumen 20 in a ratchet-like fashion.

As provided above, device 10 includes a dose indicator device. The advance tube 46 includes indicia device 102 dispose thereon (shown in FIGS. 9 and 11) visible through the at least one display port 104 defined in nozzle 12 (shown in FIGS. 16–18). Indicia device 102 comprises a strip of paper attached to the tube distal end 100, with a series of numbers, representing the number of doses, printed thereon. As the advance tube 46 rotates, the numbers are displayed through the display port 104 in sequence. While a strip of paper is used in one embodiment, other indicia devices for displaying the number of doses are contemplated. For example, the numbers could be written or printed directly upon the tube distal end 100. Furthermore, projecting members 96 could operably engage a counting device connected to an analog or digital display for displaying the number of doses administered.

Figure 16:
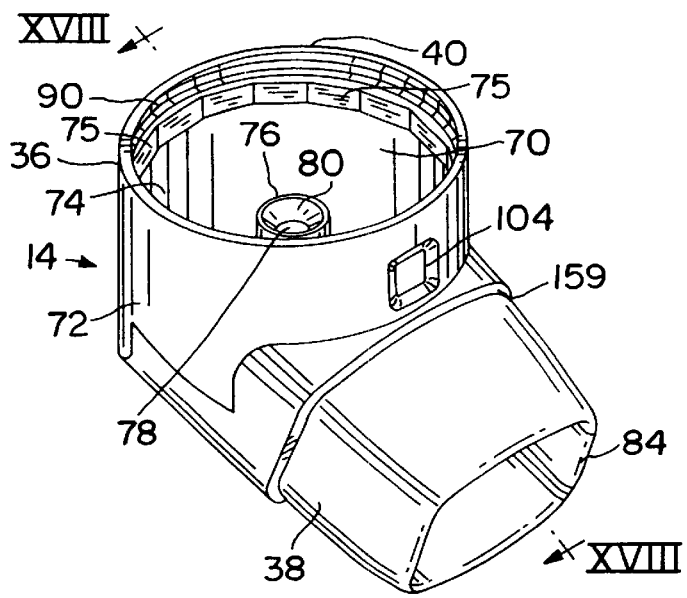
FIG. 16 is a perspective view of the nozzle of FIG. 1 removed from the housing.
Figure 17:
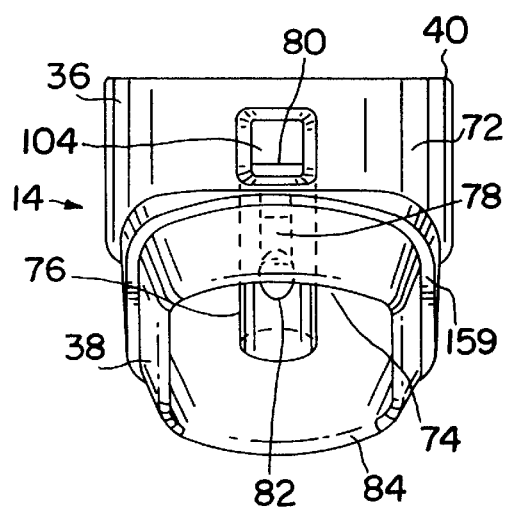
FIG. 17 is a front elevational view of the nozzle of FIG. 16.
Figure 18:
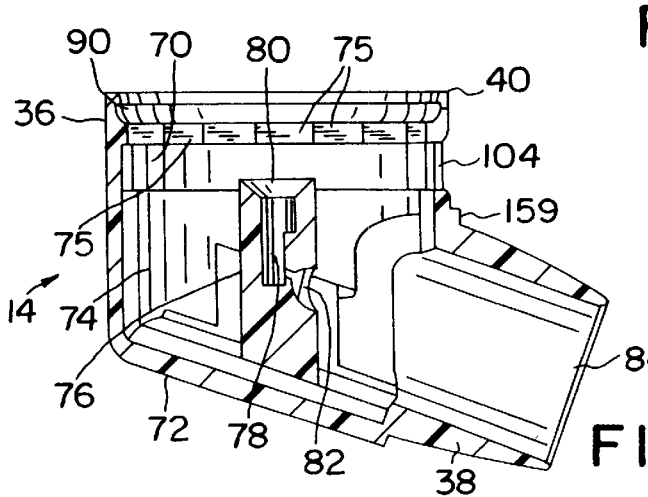
FIG. 18 is a side elevational view in cross-section of the nozzle of FIG. 16 taken substantially along line XVIII—XVIII.

Turning back to FIG. 1, it is shown that nozzle 14 is intended for insertion into the mouth of a user, although it is contemplated that inhalation device 10 could be used with any orifice of the body. Turning to FIGS. 16–18, further detail on nozzle 14 is provided. FIG. 16 shows a perspective view of the nozzle 14 removed from the housing 12, while FIGS. 17 and 18 show a front elevational and side elevational view in cross-section. It is preferred that nozzle 14 is comprised of surgical metal material or rigid plastic.

FIGS. 16–18 reveal that nozzle 14 is preferably comprised of upper and lower portions 36 and 38, in operable communication with the housing 12 and lumen 20. Upper portion 36 has a proximal end 40 snap-fitted to the distal end 24 of housing 12, so that the nozzle 14 is in fluid communication with the lumen 20. Although a snap-fit is described, any means for connecting the nozzle 14 to the housing 12 is contemplated. The at least one display port 104 is defined in the upper portion 36 of the nozzle 12 in fluid communication with the nozzle lumen 74 and in spaced and positional relationship with the advance ring 94.

Provision is further made for removably connecting the nozzle 14 to the housing 12, so that the nozzle 14 is in removable, rotatable, operable communication with the lumen 20. FIGS. 16 and 18 show that the nozzle 14 includes nozzle inner and outer surfaces 70 and 72, respectively, and the nozzle lumen 74 is defined by nozzle inner surface 70 so that the nozzle lumen 74 is in fluid communication with the lumen 20. While only one nozzle lumen 74 is shown, a plurality thereof are contemplated, substantially co-axially aligned with each other and all in fluid communication with the lumen 20.

As provided, extended ring portion 86 is formed at distal end 24 of housing 12. Ideally, the extended ring portion 86 is joined to and integral with the housing 12 and is utilized to secure the nozzle 14 to the housing 12 in a snap fit manner so that the nozzle 14 is in fluid communication with the lumen 20. Extended ring portion 86 is formed with at least one lip 88 projecting generally radially outwardly from the extended ring portion 86, and extending around the circumference thereof. While one lip 88 is shown, two or more lips 88, or even a plurality of generally radially outwardly extending nubs, are contemplated.

At least one annular groove 90 (best seen in FIGS. 16 and 18) extends around the inner circumference of nozzle proximal end 40 in spaced relationship and positionally alignment with the lip 88. The groove 90 is formed to receive lip 88 of the housing 12, so that the groove 90 and lip 88 act in concert to secure the nozzle 14 to the housing 12 in an air-tight, snap-type friction fit. Again, while this snap-type friction fit is preferred, other securing means are contemplated.

Further, as provided previously, extended ring portion 86 is formed with a plurality of panels 87 in numerical and positional relationship to panels 75 in nozzle 14. In one preferred embodiment, extended ring portion 86 and nozzle 14 both include eighteen panels 87 and 75 respectively. The panels 87 and 75 cooperate to provide a slight friction that allows the nozzle 14 to rotate about housing 12, similar to that of a watch bezel. Rotating the nozzle 14 allows the dose indicator device to be reset at the end of each predetermined period, whether daily, weekly, monthly, etc, where the interaction between panels 75 and 87 prevents such reset from occurring accidentally.

Support 76 is provided in nozzle 14 with the one passageway 78 defined therein (best seen in FIG. 18 but also shown in phantom in FIG. 17) in fluid communication with the lumen 20, so that the medicament dispenser 26 can be supported and located therein. In one preferred embodiment, support 76 defines first and second openings 80 and 82, respectively, with passageway 78 in fluid communication with and extending therebetween. As best seen in FIG. 18, the first opening 80 is in proximity to and in fluid communication with the lumen 20, while the second opening is in proximity to and in fluid communication with the nozzle lumen 74.

If the inhalation device 10 is used with medicament dispenser 26, the protruding portion or outlet valve member (not shown) of the medicament dispenser 26 is inserted into the first opening 80 and the passageway 78, so that the dispenser is supported by support 76. The protruding portion of the medicament dispenser 26 can be depressed to move the dispenser 26 relative to the nozzle, opening a valve in the medicament dispenser 26 so that a premeasured dose of medicament is discharged. One dose of medicament will be discharged each time the dispenser 26 is fully depressed. The medicament is discharged into the passageway 78 through the second opening 82 into the nozzle lumen 74 from which it can be inhaled or otherwise ingested by the user through the nozzle opening 84.

Figure 19:
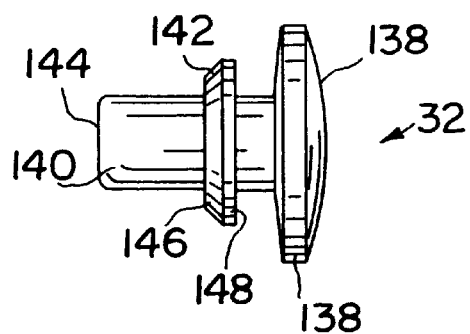
FIG. 19 is a side elevational view of the pointer of FIG. 1.

The relationship of the level display device 32 to the level indicator 30 will be better understood by turning to FIG. 19. FIG. 19 shows a side elevation view of the level display device 32, which in one preferred embodiment is a pointer 136 comprised of surgical metal material or rigid plastic.

Pointer 136 ideally consists of a rounded upper portion 138, which is generally circular when viewed from the front, and post member 140 extending therefrom and integral therewith. While a circular shape is shown, other shapes are contemplated including, for example, diamonds and arrows. Pointer 136 further includes at least one lip 142 projecting generally radially outwardly from post member 140 and extending around the circumference thereof While one lip 142 is shown, two or more lips 142 or even a plurality of generally radially outwardly extending nubs are contemplated.

As shown, post member 140 has a predetermined outer circumference such that a distal end 144 can extend through the slot 34 and operably engage helically wound groove 54. Lip 142 is positionally spaced from the upper portion 138 so that the pointer 136 can slidably move in slot 34 in a linearly reciprocal fashion. Lip 142 is further formed having angled and engaging surfaces 146 and 148. Angled surface 146 is formed so that it can readily pass through the slot 34 into the lumen 20, where an engaging surface 148 then slidingly engages inner surface 18 of the housing 12.

When advance tube 46 is inserted into the lumen 20, the pointer 136 is inserted through the slot 34 to operably engage the helically wound groove 54. Lip 142 is sufficiently flexible to pass through the slot 34. Pointer 136 is advanced through the slot 34 until the distal end 144 operably engages the helically wound groove 54 in a snap-fit fashion so that the engaging surface 148 engages the inner surface 18. The interaction of distal end 144 with the helically wound groove 54 and engaging surface 148 with the inner surface 18 are sufficient to hold the pointer 136 in place in slot 34. As the advance tube 46 advances and moves rotationally in lumen 20, the operable association of the distal end 144 and the helically wound groove 54 causes the pointer 136 to slidably move in the slot 34 in a linear fashion. This movement of the pointer 136 is indicative of the amount of medicament remaining in the medicament dispenser 26. FIGS. 1 and 5 show the slots 34 includes mountings 33, which assist the user in determining how much medicament remains.

Figure 19A:
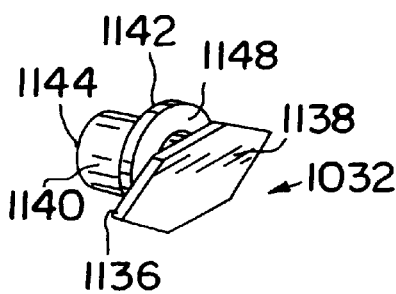
FIG. 19A is a perspective view of an alternate embodiment of the pointer of FIG. 19.

FIG. 19A depicts an alternate embodiment of the pointer 136 of FIG. 11. Correspondingly, the last three digits in the 1000 series of numerals depicted in FIG. 19A are connected to elements which have the same function and/or structure as those described with regard to FIG. 19. In FIG. 19A, upper portion 1138 of the level display device 1032, i.e., the pointer 1136, is depicted as a double arrow.

Figure 20:
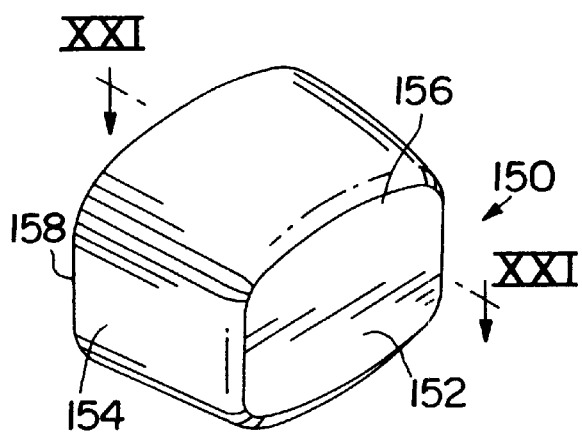
FIG. 20 is a perspective view of the replaceable cap that removably engages the nozzle of the inhalation device of FIG. 1 and is removed therefrom.
Figure 21:
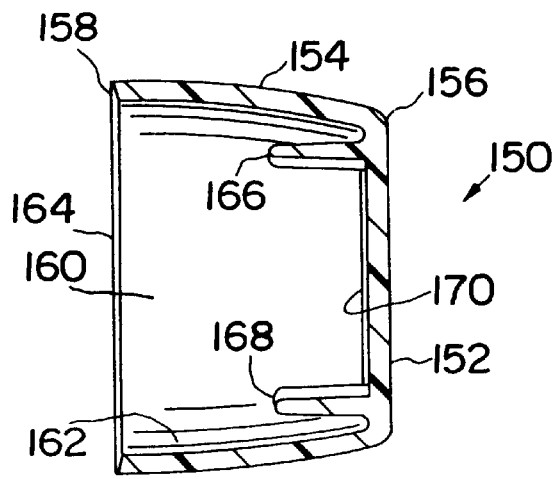
FIG. 21 is a side elevational view in cross-section of the cap of FIG. 20 taken substantially along line XXI—XXI.

Turning now to FIGS. 20 and 21, a replaceable cap 150 is shown for removable and replaceable use with nozzle 14. FIGS. 20 and 21 show a perspective view and side elevational view in cross section of cap 150. It is contemplated that replaceable cap 150 is formed of surgical metal material or rigid plastic suitable for sterilization and reuse or disposal.

In one preferred embodiment, the replaceable cap 150 has a generally trapezoidal shape when viewed from the end; however, other shapes are contemplated. Replaceable cap 150 is formed so that it engages the distal end of the nozzle 14 at the nozzle opening 84 forming a tight friction fit therewith. A generally flat lid 152 is included in the cap 150 with a skirt 154 extending from a peripheral edge 156 thereof The skirt 154 is further formed with a lower cap edge 158 which abuts against shoulder 159 defined in the nozzle 14.

A chamber 160 is defined in cap 150 by an inner surface 162, while an opening 164 is defined opposite the lid 152 by the lower cap edge 158. At least two lips, first and second lips 166 and 168, project generally inwardly from a lid inner surface 170. While two lips 166 and 168 are shown, three or more lips are contemplated. Furthermore, it is contemplated that replaceable cap 150 could be attached by other means including threads, clasps, pins, etc. In the preferred embodiment, the opening 164 is configured to receive the distal end of the nozzle 14, with first and second lips 166 and 168 configured to have a tight friction fit with the nozzle outer surface 72.

In operation as a reusable device 10, the medicament dispenser 26 must be inserted into the device 10. In one embodiment, device 10 is disassembled so that the medicament dispenser 26 can be inserted. First, advance tube 46 must be removed from the tube lumen 20. This requires that top member 42 be removed from the distal end 24 and the pointer 136 be removed from the slot 34, so that the advance tube 46 containing the advance ring 94 can be removed from the housing 12. Note that concave engaging portion 35 assists the user in removing the pointer 136.

The user can now reassemble the inhalation device 10 to incorporate the medicament dispenser 26, if desired. Medicament dispenser 26 is operably associated with the advance ring 94. This is preferably accomplished by inserting the outlet valve member of the medicament dispenser 26 into the aperture 124 so that the proximal end of the medicament dispenser 26 is in contact with the inner surface 128 and contained in the cup-like structure defined by the inner surface 128 and the ring portion 122. The medicament dispenser 26, and advance ring 94 can now be operably associated with the advance tube 46. Furthermore, if the inhalation device 10 is used with medicament dispenser 26, the protruding portion or outlet valve member (not shown) of the medicament dispenser 26 is inserted into first opening 80 and passageway 78, so that the dispenser is supported by the support 76. However, it is also contemplated that the inhaler device 10 is disposable, wherein the device 10 is sold with the dispenser 26 already disposed therein and with advance ring 94 fixedly connected to dispenser 26.

While not preferred, it is contemplated that advance ring 94 is removed from tube lumen 48. In this embodiment, medicament dispenser 26 and advance ring 94 are inserted into the tube lumen 48. In the embodiment shown in FIGS. 9 and 10, three grooves 58 are defined in and equally spaced about the inner surface 60 partially along the longitudinal axis of the advance tube 46. The advance ring 94, preferably including the medicament dispenser 26, is placed in the tube lumen 48 so that the projecting member 96 operably engages the groove 58. Projecting member 96 is preferably in spaced relationship to the groove 58, so that the advance ring 94 slidably advances in the tube lumen 48 in a linear fashion until the projecting member 96 operably engages the serrated portion 98.

When the advance tube 46 is inserted into the lumen 20, the pointer 136 is inserted through the slot 34 to operably engage the helically wound groove 54. As shown, the post member 140 has a predetermined outer circumference such that distal end 144 can extend through the slot 34 and operably engage the helically wound groove 54. Lip 142 is sufficiently flexible to pass through the slot 34. The pointer 136 is advanced through the slot 34 until the distal end 144 operably engages the helically wound groove 54 in a snap-fit fashion so that the engaging surface 148 engages the inner surface 18. The interaction of distal end 144 with the helically wound groove 54 and engaging surface 148 with the inner surface 18 is sufficient to hold the pointer 136 in place in slot 34.

Top member 42 may now be replaced. Top member 42 is operably associated with at least the housing 12 so that ring portion 62 is in contact with and rests upon the proximal end 22, while the skirt portion 64 extends into the lumen 20. Extending member 66 operably engages at least one housing groove 68 (best seen in FIG. 5) defined in the inner surface 18, so that at least the medicament dispenser 26 is securably movably mounted and properly centered in the lumen 20. Moreover, a locking slot in fluid communication with the housing groove 68 is contemplated for locking top member 42 in position.

In another embodiment, it is contemplated that advance ring 94 is retained within advance tube 46, and tube 46 remains in lumen 20 in operable association with both the top member 42 and pointer 136. In this embodiment, dispenser 26 is inserted through the aperture 63 into the tube lumen 48. Aperture 63 and ring portion 62 ensure proper placement of the dispenser 26. The outlet valve member of the medicament dispenser 26 is inserted into the aperture 124 so that the distal end of the medicament dispenser 26 is in contact with the inner surface 128 and contained in the cup-like structure defined by the inner surface 128 and the ring portion 122. In this manner, the protruding portion of the outlet valve member (not shown) of the medicament dispenser 26 is inserted into first opening 80 and passageway 78, so that the dispenser is supported by the support 76.

The protruding portion of the medicament dispenser 26 can be depressed (downwardly) to move the dispenser 26 relative to the nozzle, opening a valve in the medicament dispenser 26 so that a premeasured dose of medicament will discharge. One dose of medicament will be discharged each time the dispenser 26 is fully depressed. The medicament is discharged into the passageway 78 through the second opening 82 into the nozzle lumen 74 from which it can be inhaled or otherwise ingested by the user through the nozzle opening 84.

Preferably advance tube 46, which is rotatably disposed within the tube lumen 48, has the projecting members 96 operably engaging the teeth 118 of the serrated portion 98. Downward pressure on the advance ring 94 causes the three projecting members 96 to move into, and press downwardly on, the grooves 120 defined in the serrated portion 98 by teeth 118. Releasing the pressure on the advance ring 94 causes the projecting members 96 to move towards the tip of the next tooth and groove in the series of teeth 118 and grooves 120, in a rachet-like fashion. Furthermore, as the three projecting members 96 engage the grooves 120, it causes the advance tube 46 to rotate in the lumen 20 in the opposite direction in a rachet-like fashion.

As the advance tube 48 advances and moves rotationally in the lumen 20, the operable association of the distal end 144 and the helically wound groove 54 causes the pointer 136 to slidably move in the slot 34 in a linear fashion. This movement of the pointer 136 is indicative of the amount of medicament remaining in the medicament dispenser 26. Further, as the advance tube 46 rotates, the indicia device 102 rotates, indicating the number of doses administered during a predetermined period. At the end of such period, nozzle 14 can be rotated until the first number, preferably 0, is visible in display port 104. This acts to reset the dose indicator device.

After all the medicament is dispensed from the dispenser 26, the dispenser 26 may be removed from tube lumen 48 and discarded, if device 10 is reusable. However, it is also contemplated that device 10 is disposable, wherein both the dispenser 26, housing 12, nozzle 14 and cap 150 are discarded. The level indicator device 30 may be reset by rotating advance tube 46 in the counter-advance direction, i.e., opposite to that of the normal advance rotation. In turn, this will cause the level display device 32 to return to its original position in slot 34 in a linear fashion. The inhalation device 10 is now ready for reuse.

Although the prior art has been described with reference to certain preferred embodiments, numerous modifications and variations can be made by those skilled in the art without departing from the novel spirit and scope of this invention.

What is claimed is:

1. An inhalation device for dispensing a medicament comprising:

a housing defining a lumen;

a level indicator device disposed in said lumen operably associated with said housing for linearly indicating a remaining amount of the medicament; and a dose indicator device operably associated with said level indicator device for indicating a number of doses dispensed, said level indicator device including an advance tube that is rotatably disposed within said lumen, and that has at least one helically wound groove formed on an outer surface thereof.

2. The device of claim 1 further comprising a reset device operably associated with at least said dose indicator device, whereby said dose indicator device may be reset.

3. The device of claim 1 further comprising a top member operable associated with at least a proximal portion of said housing.

4. An inhalation device for dispensing a medicament comprising:

a housing defining a lumen;

a level indicator device disposed in said lumen operably associated with said housing for linearly indicating a remaining amount of the medicament;

a dose indicator device operably associated with said level indicator device for indicating a number of doses dispensed; and a reset device operably associated with at least said dose indicator device, whereby said dose indicator device may be reset;

said reset device comprising a nozzle operably associated with said housing and in fluid communication with said lumen.

5. The device of claim 4 wherein said nozzle includes a replaceable cap engaging a distal end of said nozzle, said cap forming a tight friction fit with said nozzle distal end.

6. The device of claim 4 wherein said nozzle further includes a proximal end snap-fitted to a distal end of said housing in a rotatable manner and in fluid communication with said lumen.

7. The device of claim 4 wherein said nozzle defines at least one passageway therein in fluid communication with at least said lumen.

8. An inhalation device for dispensing a medicament comprising:

a housing defining a lumen;

a level indicator device disposed in said lumen operably associated with said housing for linearly indicating a remaining amount of the medicament; and a dose indicator device operably associated with said level indicator device for indicating a number of doses dispensed;

said level indicator device including an advance device movably disposed within said lumen of said housing.

9. The device of claim 8 wherein said advance device is rotatably disposed within said lumen of said housing.

10. The device of claim 8 wherein said advance device is an advance tube having at least one helically wound groove formed on an outer surface thereof and rotatably disposed within said lumen of said housing.

11. The device of claim 10 wherein said level indicator device further includes at least one level display device operably associated with said advance tube and said housing.

12. The device of claim 11 wherein said housing defines at least one slot with said at least one level display device movably disposed therein in a linear fashion and operably associated with said at least one groove.

13. The device of claim 8 wherein said advance device includes an advance member disposed in said lumen of said housing in operable communication therewith.

14. The device of claim 13 wherein said advance member comprises an advance ring disposed within said lumen and operably associated with said advance device.

15. The device of claim 14 wherein said advance ring is operably associated with at least one serrated portion defined in said advance device.

16. The device of claim 8 wherein said dose indicator device includes an indicia device operably associated with said advance device.

17. An inhalation device with a medicament dispenser for dispensing a medicament, comprising:

a housing defining a lumen containing the medicament dispenser;

a level indicator device disposed in said lumen and operably associated with said housing, for indicating an amount of the medicament in the medicament dispenser;

a dose indicator device operably associated with said level indicator device for indicating a number of doses of the medicament dispensed; and a nozzle removably connected to a distal end of said housing in a rotatable manner and in fluid communication with the medicament dispenser for dispensing the medicament, whereby said nozzle is operably associated with said dose indicator device so that said dose indicator device may be reset.

18. The device of claim 17 wherein said nozzle includes a replaceable cap engaging a distal end of said nozzle, said cap having a tight friction fit with said nozzle distal end.

19. The device of claim 17 wherein said nozzle further includes a proximal end snap-fitted to said distal end of said housing and in fluid communication with said lumen.

20. The device of claim 19 wherein said nozzle defines at least one passageway therein in fluid communication with at least said lumen and said nozzle distal end.

21. The device of claim 20 wherein said level indicator device includes an advance tube rotatably disposed within said lumen of said housing.

22. The device of claim 21 wherein said advance tube includes at least one helically wound groove formed on an outer surface thereof.

23. The device of claim 22 wherein said level indicator device further includes at least one level display device operably associated with said advance tube and said housing.

24. The device of claim 23 wherein said housing defines at least one slot with said at least one level display device linearly movably disposed therein and operably associated with said at least one groove.

25. The device of claim 24 wherein said level indicator device further includes an advance ring disposed in said lumen of said housing operably associated with said advance tube.

26. The device of claim 25 further including said advance tube defining a serrated portion and said advance ring is disposed in a lumen of said advance tube operable associated with said serrated portion.

27. The device of claim 26 wherein said advance ring includes three projecting members equally spaced thereabout and operably associated with said serrated portion.

28. The device of claim 27 wherein said dose indicator device includes an indicia device operably associated with said advance tube, whereby a number of doses of medicament are indicated for a predetermined period.

29. The device of claim 28 wherein said nozzle defines at least one port therein for displaying said indicia device.

30. The device of claim 29 further comprising a top member operably associated with at least a proximal end of said housing, whereby the medicament dispenser is properly positioned within said lumen.

* * * * *